US00PP31166P2

(12) United States Plant Patent
Van Swieten

(10) Patent No.: US PP31,166 P2
(45) Date of Patent: Dec. 3, 2019

(54) ***PHALAENOPSIS* ORCHID PLANT NAMED 'PHALUSYL'**

(50) Latin Name: ***Phalaenopsis* hybrid**
Varietal Denomination: PHALUSYL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,813

(22) Filed: Jan. 15, 2019

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
CPC ..... A01H 5/02; A01H 6/62
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALUSYL', particularly characterized by having light greenish-yellow, spotted flowers with small red-purple lips, 1 to 4 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALUSYL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALUSYL'.

The new *Phalaenopsis* plant is a product of a planned breeding program conducted by the inventor in Bleiswijk, The Netherlands. The objective of this breeding program was to create a new *Phalaenopsis* plant with numerous attractive light greenish-yellow, spotted flowers with small red-purple lips, suitable for potted plant production.

The new *Phalaenopsis* plant 'PHALUSYL' is a result of cross-pollination made by the inventor in May 2005 in Bleiswijk, The Netherlands, of the proprietary female, or seed parent, *Phalaenopsis* hybrid '01-1684' (unpatented) with the proprietary male, or pollen parent, *Phalaenopsis* hybrid '22964-01' (unpatented).

The new *Phalaenopsis* was selected by the inventor as a single plant within the progeny of the stated cross-pollination in a controlled greenhouse in Bleiswijk, The Netherlands, in August 2008. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALUSYL' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALUSYL' as a new and distinct variety of *Phalaenopsis* plant:

1) Light greenish-yellow, spotted flowers with small red-purple lips;
2) 1 to 4 peduncles;
3) Peduncle is medium long and moderate; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in December 2018. Colors in the photographs may differ from the color values cited in the detailed botanical description, which accurately describe the actual colors of the new variety.

DESCRIPTION OF THE NEW VARIETY

Figure 1:
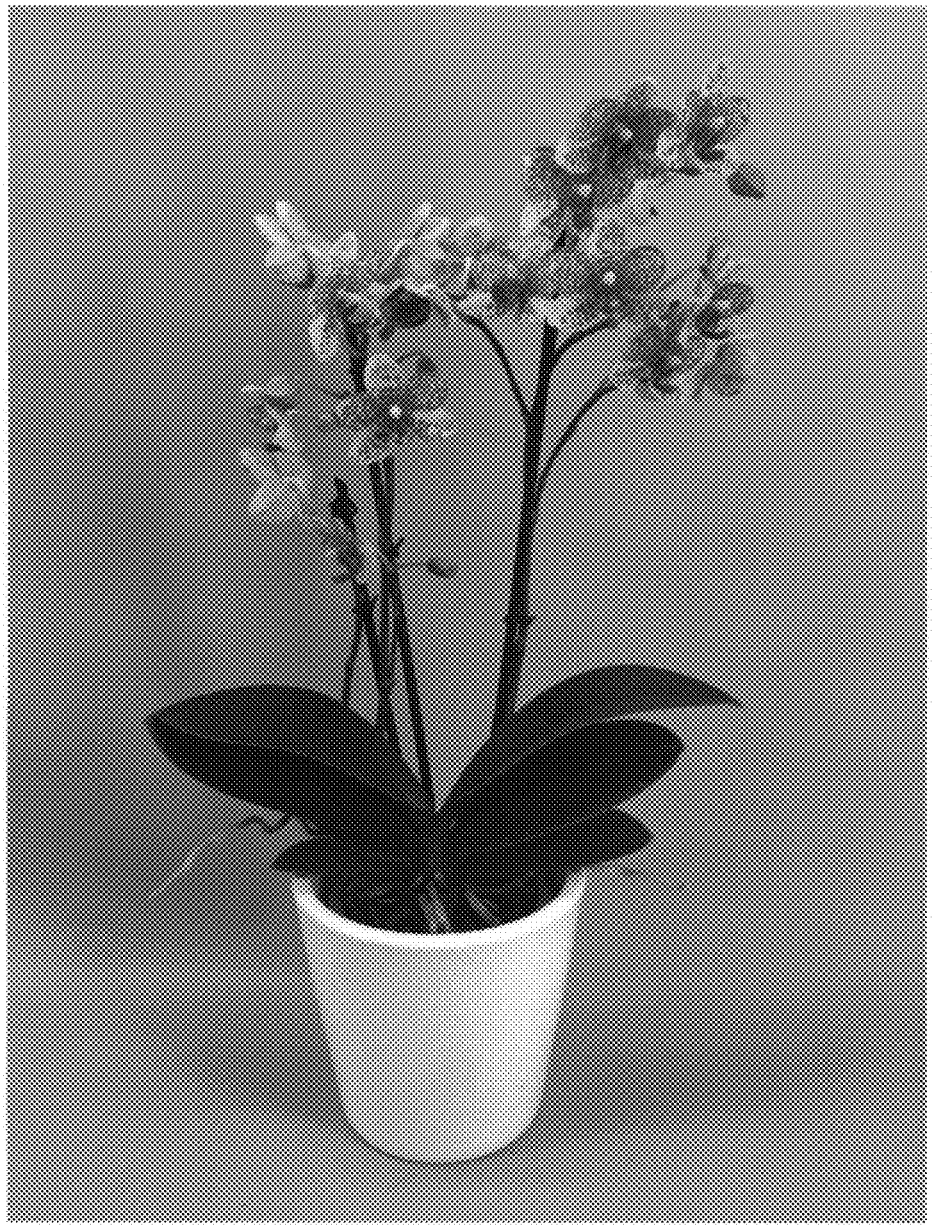
FIG. 1 shows the overall plant habit, including blooms, buds and foliage of 'PHALUSYL'.
Figure 2:
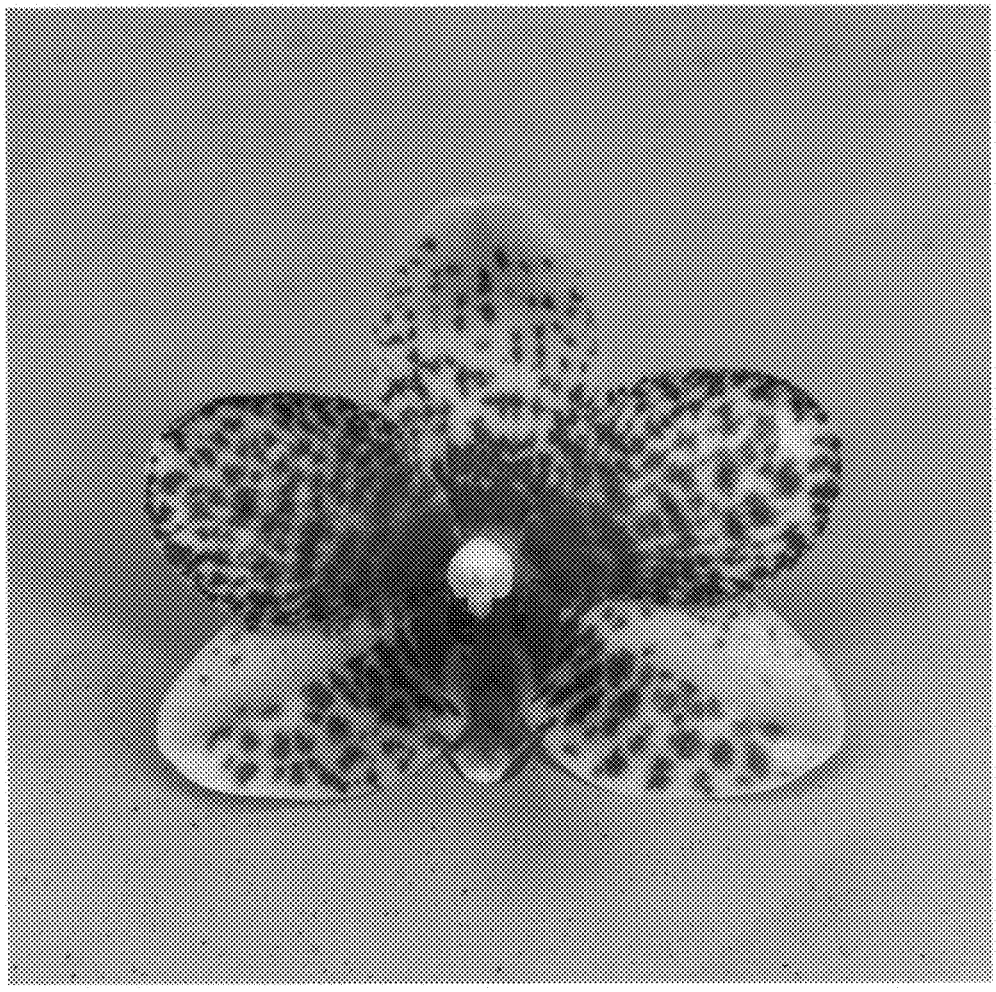
FIG. 2 shows a close-up of a flower of 'PHALUSYL'.
Figure 3:
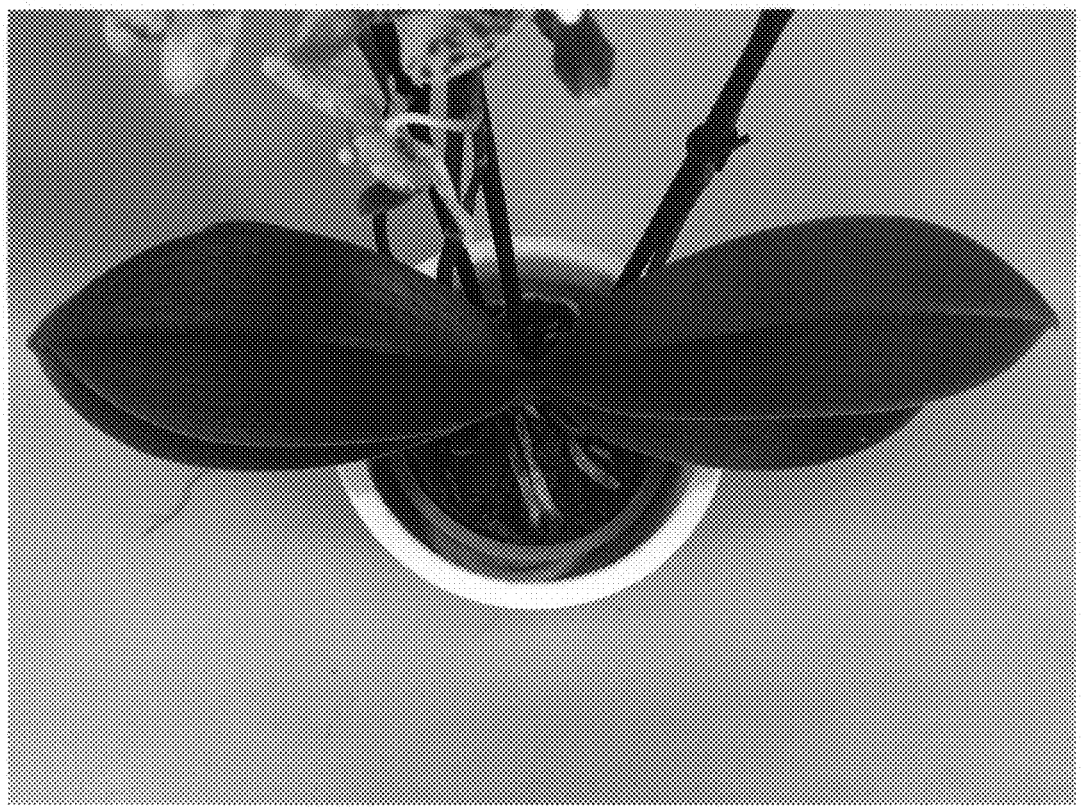
FIG. 3 shows an overhead view of the leaves of 'PHALUSYL'.

The following detailed description sets forth the distinctive characteristics of 'PHALUSYL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in December 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12 centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALUSYL'.

Parentage:

*Female parent*.—*Phalaenopsis* cultivar '01-1684' (unpatented).

*Male parent*.—*Phalaenopsis* cultivar '22964-01' (unpatented).

Propagation:

*Type*.—Meristem tissue culture.

Roots:

*Root description*.—Greyed-green (RHS 190B/C) colored roots with branching lateral roots having yellow-green (RHS 145A) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with panicle inflorescence.

*Height* (*from soil level to top of inflorescence*).—Approximately 37.0 cm to 42.0 cm.

*Width* (*measured from leaf tips*).—About 28.0 cm to 30.0 cm.

*Vigor*.—Moderate.

Leaves:

*Mature leaves*.—Quantity per plant: 8 to 10 leaves are produced before flowering. Length (fully expanded): 15.0 cm to 17.0 cm. Width: 5.5 cm to 6.5 cm. Shape: Oblong. Base shape: Moderately elongated. Apex: Acute unequal. Leaf blade angle with the petiole (measured from the horizontal position): Between 25 degrees and 35 degrees. Leaf margin: Entire. Color: Upper surface: RHS 146A. Lower surface: RHS 146B. Texture (upper surface): Rough. Thickness: 2.3 mm to 2.7 mm. Venation: Pattern: Parallel. Color of the midvein: Upper surface: RHS 147A. Lower surface: RHS 146B.

Peduncle:

*Quantity per plant*.—1 to 4.

*Number of flowers per peduncle*.—12 to 17.

*Length*.—37.0 cm to 42.0 cm.

*Diameter*.—4.4 mm to 4.8 mm.

*Strength*.—Strong.

*Aspect*.—Upright to slightly pendant.

*Texture*.—Smooth.

*Color*.—Green (RHS 146B).

*Internode length*.—5.0 cm to 7.0 cm.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 210.0 mm to 270.0 mm.

*Flowering time*.—First flowers can be expected 10 to 11 months after planting in a 12 cm (diameter) pot.

*Flower*.—Height: 53.0 mm to 58.0 mm. Diameter: 55.0 mm to 60.0 mm. Depth of lip: 18.0 mm to 19.0 mm.

*Flower longevity*.—On the plant: 15 to 24 weeks.

*Fragrance*.—Absent.

*Flower bud*.—Average size: Large. Length: 18.0 mm to 20.0 mm. Width: 13.0 mm to 15.0 mm. Shape: Egg shaped. Color: Green (RHS 144C) with diluting dark purplish-red spots (RHS N79B).

*Petals*.—Arrangement: Open/free. Shape: Semi-circular. Apex: Rounded asymmetric. Margin: Slightly undulated. Length (from base to tip): 26.0 mm to 28.0 mm. Width: 22.0 mm to 25.0 mm. Color (when fully opened): Upper surface: Basic color: Light yellow-green (RHS 145C). Over color: Purplish-red spots (RHS 71A). Lower surface: Basic color: Very light yellow-green (RHS 145D). Over color: Diluting purplish-red spots (RHS 71A).

*Dorsal sepal*.—Shape: Elliptic. Apex: Emarginated asymmetric. Margin: Entire. Length (from base to tip): 28.0 mm to 30.0 mm. Width: 26.0 mm to 28.0 mm. Color (when fully opened): Upper surface: Basic color: Light yellow-green (RHS 145B/C). Over color: Purplish-red spots (RHS 59B). Lower surface: Basic color: Yellow-green (RHS N144D). Over color: Diluting purplish-red spots (RHS 59B).

*Lateral sepals*.—Shape: Ovate. Apex: Obtuse asymmetric. Margin: Entire. Length (from base to tip): 29.0 mm to 31.0 mm. Width: 20.0 mm to 22.0 mm. Color (when fully opened): Upper surface: Basic color: Light yellow-green (RHS 145C). Over color: Purplish-red (RHS 71A) at the base; purplish-red spots (RHS 59B). Lower surface: Basic color: Light yellow-green (RHS 145C). Over color: Yellow-green (RHS 145B) toward the tip and purplish-red spots (RHS 59B).

*Labellum* (*lip*).—Whiskers: Absent.

*Lateral lobe*.—Shape: Type I (as described in the International Union for the Protection of New Varieties of Plants (UPOV) Test Guidelines for *Phalaenopsis*); ligulate. Margin: Undulated. Length: 10.0 mm to 12.0 mm. Width: 3.0 mm to 5.0 mm. Color: Yellow (RHS 14B) at the base; purplish-red (mix of RHS 61A and 59B).

*Apical lobe*.—Shape: Obtrullate. Margin: Entire. Length: 14.0 mm to 16.0 mm. Width: 8.0 mm to 10.0 mm. Color: Red (RHS 185A) at the base; dark red (RHS 59A) and reddish-purple (RHS N78A) toward tips.

*Callus*.—Average size: Small. Height: 3.0 mm to 4.0 mm. Length: 2.0 mm to 3.0 mm. Width: 2.0 mm to 3.0 mm. Color: Dark reddish-orange (RHS 178B).

Reproductive organs:

*Column*.—Length: 8.0 mm to 10.0 mm. Diameter: 4.4 mm to 4.7 mm. Color: Light purple (RHS 76C) at the base and white (RHS NN155C) toward the tip.

*Pollinia*.—Quantity: 2. Diameter: 0.5 mm to 0.8 mm. Color: Yellow (RHS 17A).

*Ovary*.—Length: 9.0 mm to 11.0 mm. Diameter: 2.0 mm to 2.2 mm. Color: Yellow-green (RHS 144C) and light yellow-green (RHS 145D) toward the flower.

*Pedicel*.—Length: 38.0 mm to 40.0 mm. Diameter: 2.2 mm to 2.5 mm. Color: Yellow-green (RHS 144C) at the base; light yellow-green (RHS 145D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALUSYL', cultivar '01-1684' (unpatented), is no longer in existence, so a meaningful comparison cannot be made.

'PHALUSYL' differs from male parent plant '22964-01' (unpatented) in that 'PHALUSYL' has flowers with a basic color of light yellow-green and a spotted pattern, and columns that are light purple at the base and white toward the tip, whereas '22964-01' has flowers with a basic color of dark red and an even pattern, and columns that are reddish-purple. Additionally, 'PHALUSYL' has smaller flowers and narrower apical lobes than '22964-01'.

'PHALUSYL' is most similar to the commercial *Phalaenopsis* plants named 'PHALCOFALI' (unpatented) and 'PHALCROBOH' (unpatented). 'PHALUSYL' differs from the commercial variety 'PHALCOFALI' in that 'PHALUSYL' has flowers with a basic color of light yellow-green (RHS 145C) with a spotted pattern and no whiskers, whereas 'PHALCOFALI' has flowers with a basic color of yellow (RHS 12A) with a shaded and striped pattern and whiskers.

'PHALUSYL' differs from the commercial variety 'PHALCROBOH' in that 'PHALUSYL' has flowers with a basic color of light yellow-green (RHS 145C) with a spotted pattern and no whiskers, whereas 'PHALCROBOH' has flowers with a basic color of yellow-green (RHS 154C) with an even pattern and whiskers. Additionally, 'PHALUSYL' has smaller flowers than 'PHALCROBOH'.

I claim:

1. A new and distinct variety of *Phalaenopsis* plant named 'PHALUSYL', substantially as described and illustrated herein.

* * * * *